United States Patent [19]

Grassmann

[11] 4,010,383

[45] Mar. 1, 1977

[54] PRECIPITATION DETECTOR FOR ARRANGEMENTS WHICH CONTROL WINDSHIELD WIPERS AND/OR WASHERS, AND THE LIKE

[76] Inventor: Günter Grassmann, 3151 Eddesse Nr. 40, Germany

[22] Filed: Aug. 15, 1975

[21] Appl. No.: 605,176

[30] Foreign Application Priority Data

Aug. 17, 1974 Germany .......................... 2439590
Mar. 13, 1975 Germany .......................... 2510885

[52] U.S. Cl. .............................. 307/118; 318/483; 307/10 R
[51] Int. Cl.² .......................................... H02G 3/00
[58] Field of Search ................. 307/118, 10 R, 116; 318/483, 443, 444 WW; 15/250.02, 250.12

[56] References Cited

UNITED STATES PATENTS 3,555,289  1/1971  Sobkow .................... 307/118 UX

Primary Examiner—Herman J. Hohauser
Attorney, Agent, or Firm—Michael J. Striker

[57] ABSTRACT

The arrangement includes at least one upper and one lower cooperating sensor element, each comprised of a naked electrically conductive portion adjoining the corresponding portion of the other and together defining an interelectrode gap. The naked portions are exposed to precipitation. The naked conductive portion of the lower sensor element is comprised of upwardly projecting teeth having pointed ends closely adjoining the naked conductive portion of the upper sensor element. Water droplets occupying the interelectrode gap will tend not to cling to the electrically conductive portion of the lower sensor element because of the pointed configuration of the ends of the upwardly projecting teeth. A circuit is connected to the sensor elements and detects the existence of precipitation by detecting the interelectrode gap resistance changes which result when the interelectrode gap is occupied by water droplets, and the like, and in response to such detection generates a control signal for the windshield wiper motor and/or the windshield washer motor.

19 Claims, 10 Drawing Figures

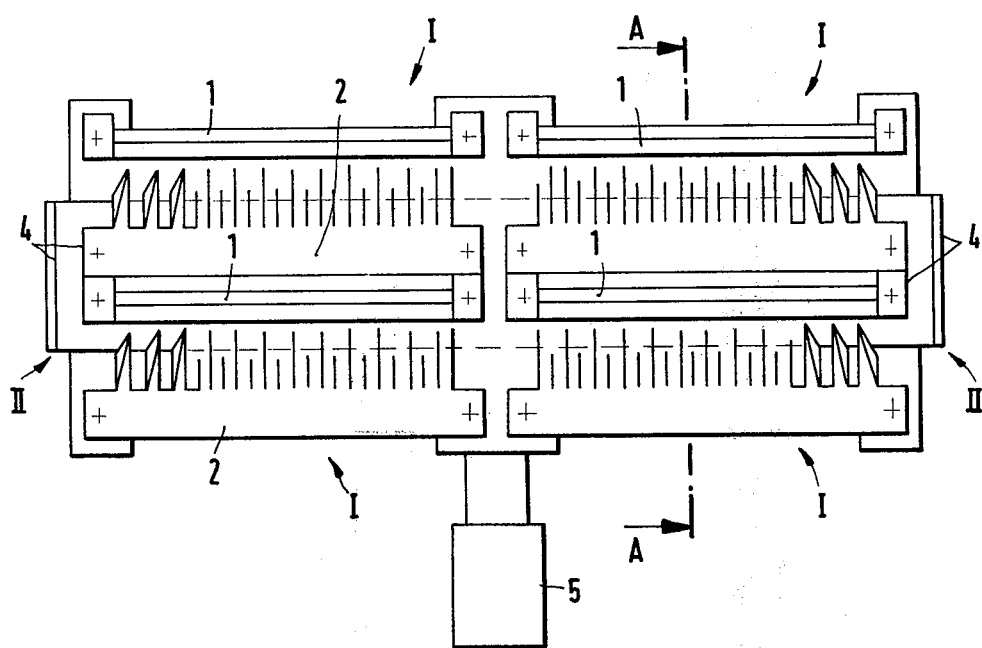
Fig. 1
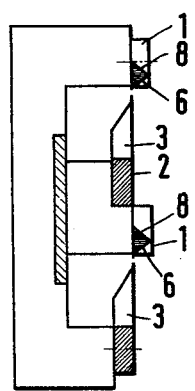 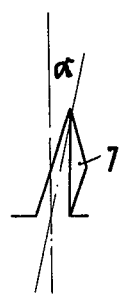 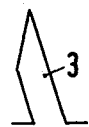
Fig. 2　　Fig. 3　　Fig. 4

PRECIPITATION DETECTOR FOR ARRANGEMENTS WHICH CONTROL WINDSHIELD WIPERS AND/OR WASHERS, AND THE LIKE

BACKGROUND OF THE INVENTION

The invention relates to arrangement in which an electronic sensor controls the operation of an electric windshield wiper motor in dependence upon the detection of electrically conductive precipitation. The sensor is comprised basically of two spaced, naked electrical conductors arranged in front of their respective mounting means so as to be freely exposed to electrically conductive precipitation. These conductors serve as sensing elements operative, as part of an electric control circuit, for generating a control signal in response to a change in the electrical resistance between them.

A sensor of this general type is disclosed in Federal Republic of Germany published patent application DT-OS No. 2,255,264. In that construction, the sensor elements are comprised of a plurality of stationary metal rods arranged in a fan-like manner. The distance and accordingly the electrical resistance between the sensor elements increases along the length of the measuring path. This sensor does in fact perform its intended function; however its sensitivity, especially in the case of changing weather conditions, is not always sufficient. It has been determined that the principal cause of the unsatisfactory operation of this known construction is that extremely small droplets became caught in the measuring path in the narrow spaces between adjoining sensor elements and, in some circumstances, cause the sensor to generate for a considerable length of time a signal indicative of a weather condition not actually in existence. It would be possible to overcome this difficulty by increasing the interelectrode spacing; however, that would in turn so greatly reduce the sensitivity of the sensor as to practically destroy its utility.

SUMMARY OF THE INVENTION

It is a general object of the invention to provide a control arrangement for a windshield wiper motor including a sensor exhibiting a faster response and greater sensitivity than known in the prior art.

This object, and others which will become more understandable from the description, below, of preferred embodiments, can be met, according to one advantageous concept of the invention, by associating with at least one upper, preferably horizontally disposed sensor element a lower comb-like sensor element whose upwardly extending comb teeth each end in a point. The pointed ends can be needle-like.

Each comb tooth point forms with the opposed sensor element a measuring section, and each individual measurement results in the generation of a certain control signal. The sharp configuration of the comb teeth produces, on the one hand, a quick runoff of water drops from the upper sensor element and, on the other hand, a quick transfer of these water drops onto the lower comb teeth. The upwardly projecting points of the comb teeth prevent the clogging of the measurement section by very small water droplets and accordingly ensure a quick response to changing weather conditions.

Alternatively, the upper sensor element can be designed bar-shaped. If this is done, then the advantages in question can be further increased by making the lower longitudinal edge of the bar-shaped sensor element—i.e., the edge adjoining the comb teeth—taper in downward and rearward direction so as to have a sharpened configuration. It is also possible to provide the bar-shaped sensor element not only with the aforementioned sharpened lower edge, but furthermore at its upper edge with an upwardly and rearwardly directed chamfer cut. In this way, the moisture falling upon the sensor is divided into one part which runs off downwardly and is used for the contact measurement and into another part which is led off upwardly as flow water. Also, this makes it possible to make the bar-shaped sensor element wider and more stable.

According to another concept of the invention, the upper sensor element can be of comb-like configuration and be provided with downwardly projecting comb teeth having pointed ends each of which stands opposite the pointed end of one of the upwardly extending comb teeth of the lower sensor element.

With this second alternative, the measuring section includes numerous comb teeth arranged in pairs of opposing teeth yielding respective measurements which are combined to form an average measurement resulting in the generation of a predetermined control signal. At the free end of each comb tooth of the upper sensor element there can be provided a catching surface extending downwards and rearwards to the pointed end of the tooth. The atmospheric moisture, or the like, caught by the catching surface is for example pushed on the aforementioned surface back and downwards to the pointed end of the comb tooth by a stream of air impinging frontally upon the sensor; from there, the drop is virtually sucked down by the oppositely positioned comb teeth ends.

If the sensor elements are oriented in vertical planes, then it is advantageous to arrange the lower sensor element rearwardly displaced relative to the upper sensor element by approximately the thickness of the material of the comb teeth. This assures that the water drops caught by the upper sensor element, due to their own weight and possibly also to the relative wind created by vehicle motion, are led off via the lower sharpened portion of the bar-shaped sensor element onto the points of the upwardly pointing comb teeth of the sensor element.

The free end of each comb tooth can be sharpened knife-like towards its rear side. The trickle transferred by the upper sensor element is then split by the knife-like portion so that the thusly achieved larger surface area utilization together with the concomitant greater adhesion force produces an accelerated draw-off of the water drop out of the measurement section. The aerodynamic characteristics can be further improved if the free end of each comb tooth has a lateral chamfer extending downwards and rearwards from the pointed end of the tooth.

The comb teeth can be arranged inclined relative to the vertical within a plane defined by the sensor elements. This makes it possible to make larger the lateral chamfers just mentioned.

For adjusting the sensor to changing apparent (vehicle-generated) wind directions, or in consideration of other factors, the sensor elements means includes be mounted pivotably on the front of the vehicle, e.g., on the hood, for pivotal movement within and/or out of a vertical plane.

According to a preferred concept of the invention, use can be made of one sensor unit having a small interelectrode gap and another sensor unit having a larger interelectrode gap. Then the sensor unit having the small gap can be used for detecting mist and light rain, and the sensor unit having the large gap can be used for detecting larger drops falling in heavy rain, the interelectrode gap resistance changes of the two units being different and thus distinguishable for the different forms of precipitation. The sensor unit having the larger gap can be comprised of two vertically extending horizontally spaced electrodes.

The sensor elements can be electrically heated to prevent the formation of ice on them.

According to an advantageous concept of the invention, use is made of a time delay circuit affording a blocking time such that a single generated control signal produces a certain number of windshield wiper operating cycles. In this way, there is assured a sufficiently long operation of the wiper, this being important for example when the wiper is activated in response to the interelectrode gap resistance change resulting from a few drops of water such as might occur when travelling through a puddle, or the like.

Advantageously the control signal derived from the sensor is also used to turn on a windshield washing arrangement.

According to an advantageous concept of the invention, one sensor unit can be continuously heated and another heated only intermittently so as to permit the formation of ice thereon. If the two sensors are otherwise of similar configuration and dimensions, the different interelectrode gap resistances thereof occurring when ice forms on the intermittently heated sensor unit can be utilized for the detection of ice.

According to another advantageous concept of the invention, each comb tooth of the lower sensor element can be provided at its pointed end with a suction conduit. These suction conduits can be connected to a sucking device and thereby contribute to a quick sucking off of small droplets from the upper sensor element down onto the lower sensor element.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 1 depicts a sensor arrangement in front view, as mounted on the hood of an automobile, for example;

FIG. 2 is a section taken on line A—A of FIG. 1;

FIG. 3 is a front view, on a larger scale, of a modified configuration of a tooth of a sensor element;

FIG. 4 is a back view of the tooth of FIG. 3;

FIG. 7b is a back view of the tooth shown in FIG. 7a;

DESCRIPTION OF THE PREFERRED EMBODIMENTS

Figure 5:
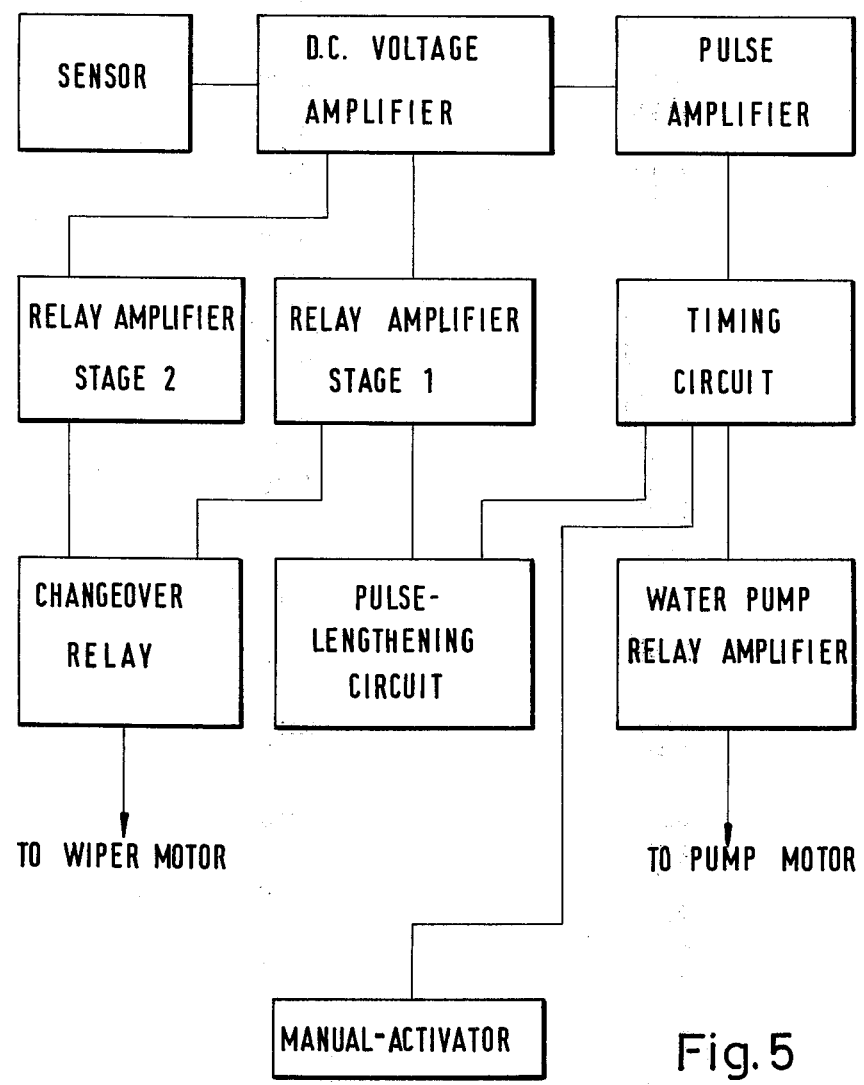
FIG. 5 is a schematic block diagram of a control arrangement for a windshield wiper and a washer arrangement.

The sensing arrangement in FIG. 1 is comprised of four sensors I. Each sensor I is comprised of an upper, horizontally disposed bar-shaped sensor element 1 which has associated with it a comb-like lower sensor element 2 whose upwardly projecting comb teeth 3 have pointed ends.

The two left sensor units I form with the two right sensor units I a flat "V" which is seen from above in FIG. 1. Electrically connected with these sensor units with relatively small electrode spacing is a sensor II with larger electrode spacing. The latter consist of two vertical electrodes 4 horizontally spaced from each other which alternatively could be arranged horizontal.

The sensing arrangement depicted in FIG. 1 can be connected to a non-illustrated mounting plug on the front side of an automotive vehicle by means of the connecting nut 5, so as to be mounted for pivotal movement within or out of a vertical plane.

FIG. 2 makes clear that the bar-shaped sensor element 2, at the longitudinal edge 6 thereof adjoining the comb teeth 3, is tapered knife-like in downward and rearward directions. Furthermore, the lower sensor element 2 is rearwardly offset relative to the associated upper sensor element 1 by a distance equal to the thickness of the comb teeth 3; as a result, water drops will be led off from the sharpened longitudinal edge 6 directly onto the pointed ends of the comb teeth 3.

The free end of each comb tooth 3 is tapered knife-like at its back side and has a lateral chamfer 7 running downwards and rearwards from the point, which is advantageous for aerodynamic reasons. In a modification of the configuration of FIG. 1, shown in FIGS. 3 and 4, the comb teeth 3 are inclined by an angle $\alpha$ relative to the vertical and are arranged within the plane formed by the sensor elements 2. This inclination would be to the left for two of the units I and to the right for the other two units I.

FIG. 5 depicts a schematic block circuit diagram of a control arrangement for the windshield washing and wiping arrangement. Even one individual and very small water drop dwelling for only a few microseconds between the sensor elements 1, 2 causes the generation of an electric voltage jump which is applied to a D.C. amplifier and to a pulse amplifier. The latter initiates the operation of a timing circuit which with a preselected blocking time of for example 1-4 controls a relay amplifier for a water pump and initiates the operation of a windshield washing arrangement. A pulse corresponding to the blocking time of the timing circuit is applied to a pulse-lengthening circuit, prolonged in the pulse-lengthening circuit by several seconds and utilized for controlling a relay amplifier stage 1 and a changeover relay.

The non-illustrated windshield wiper now runs with stage 1 for the preselected blocking time plus the prolongation created by the pulse-lengthening circuit for a time interval of several seconds. As a result, it is assured that the vehicle windshield is clean and dry.

If during the prolongation time afforded by the pulse-lengthening circuit there appears a further liquid drop on the measuring section of the sensor, then the entire cycle including the blocking time and the prolongation is initiated anew. In the illustrated schematic block circuit diagram there is provided a supplemental manual control by means of which a cycle can be manually initiated when for whatever reason a cleaning cycle for the windshield is desired.

In the event of actual rain, the rain drops, falling continually one after the other, cause the generation of a voltage jump which is applied to the D.C. voltage amplifier as a D.C. voltage signal and controls the relay amplifier for stage 1 as well as the changeover relay and initiates the operation of the non-illustrated windshield wiper motor with a correspondingly lower speed. In the event of heavy rain, there are additionally controlled a relay amplifier stage 2 as well as the changeover relay, so that the windshield wiper motor will then operate with a correspondingly higher speed. Additional such stages can be provided.

Figure 6:
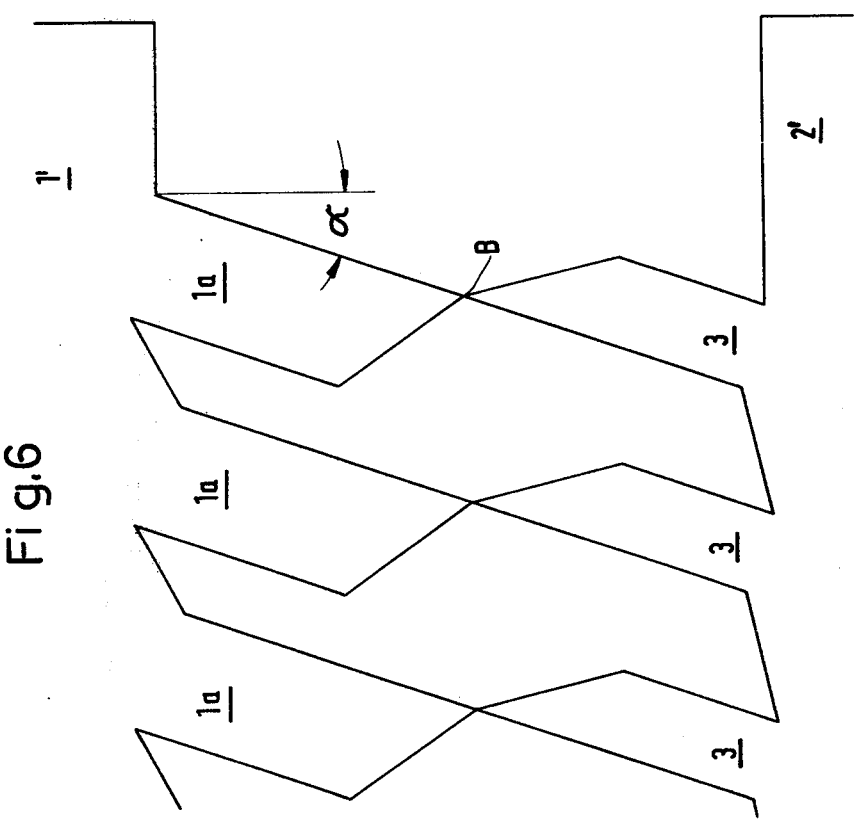
FIG. 6 is a front view of part of a sensing structure of different configuration.

The electronic sensor of FIG. 6 is comprised of an upper horizontally arranged sensor element 1' of comb-like configuration with which is associated a correspondingly configured sensor element 2'. The comb teeth 1a of the upper sensor element 1' end in lower points A, and are arranged opposite to respective upwardly projecting points B of the comb teeth 3 of the lower sensor element 2'.

Figure 7A:
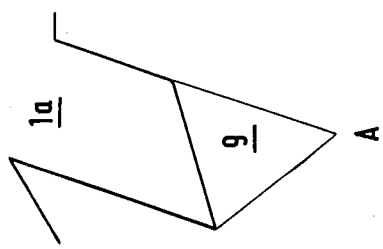
FIG. 7a is a front view of a tooth of the upper sensing element of FIG. 6.
Figure 7B:
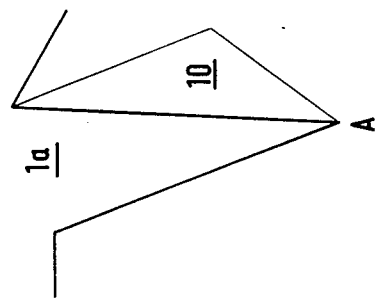

FIG. 7a shows that at the free end of each upper comb tooth 1a there is provided a catching surface 9 which extends downwards and rearwards to the point A. Lying opposed to the latter on the back side of each upper comb tooth 1a is back taper 10 (see FIG. 7b).

Figure 8:
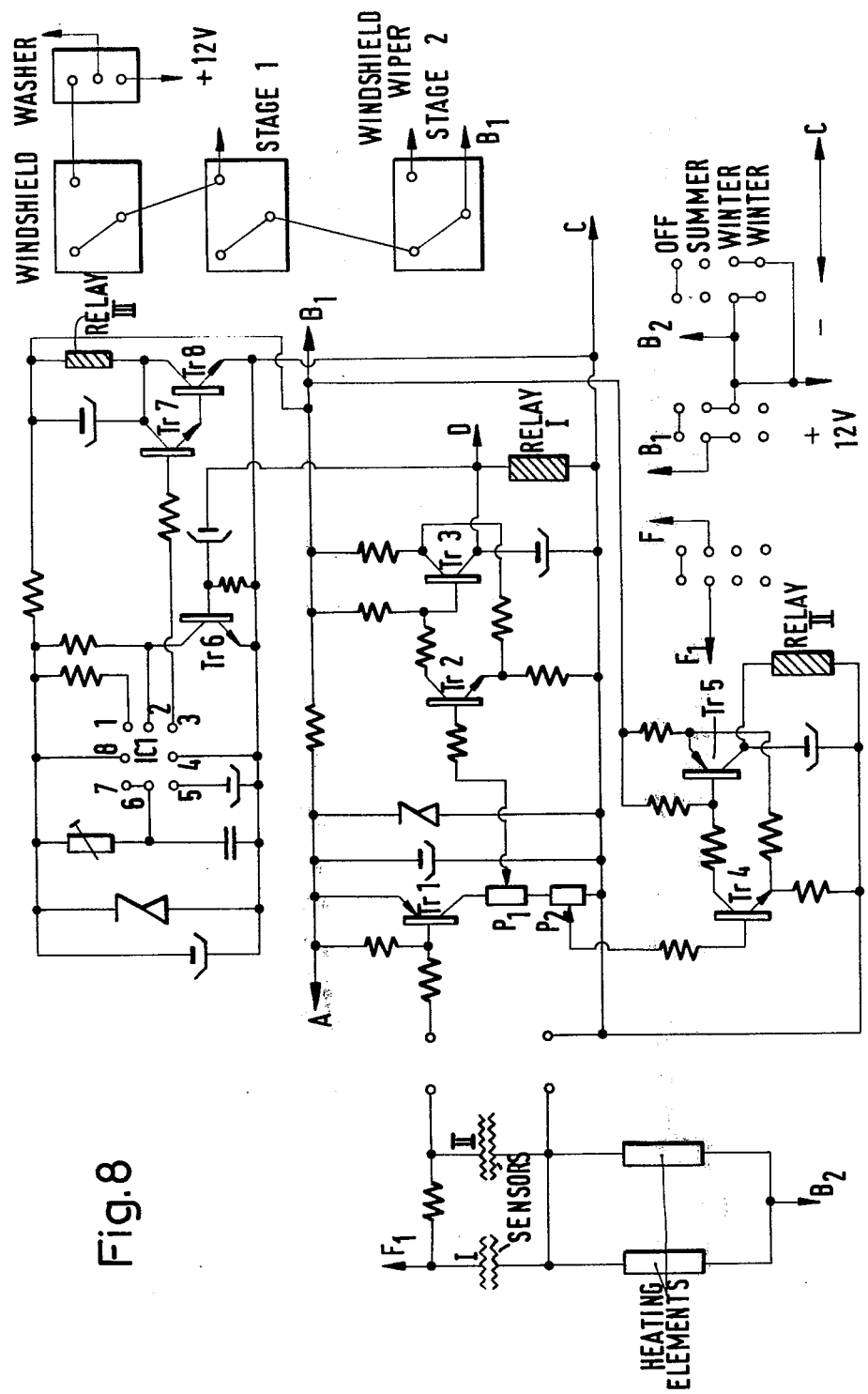
FIG. 8 is an electronic windshield wiper motor control circuit.

In FIG. 8 there is depicted a sensor I having a small electrode spacing connected via a resistor with a sensor II having a large electrode spacing.

The small droplets of mist and light rain cause the electrodes of sensor I to have an interelectrode resistance. The larger drops of heavy rain can produce at the electrodes of sensor II an interelectrode resistance which is lower than that effect at the sensor I.

The D.C. voltage amplifier comprised of transistor Tr 1 converts the resistance change appearing at the sensors into a voltage change at the regulators P1 and P2. These regulators serve for adjusting the sensitivity of the sensors.

Regulator P1 controls the multivibrator comprised of transistors Tr 2 and Tr 3 with the relay I and cause the slow windshield wiper stage to run. Shortly before this, a windshield washing arrangement has been operative for 1–4 seconds to prevent a dry running or smearing of the windshield. The control of the windshield washing arrangement is taken over by IC 1, the transistors Tr 6, Tr 7, Tr 8 and relay III.

Larger rain drops at sensor II control, via the regulator P2, the multivibrator Tr 4 and Tr 5 with the relay II the fast running windshield wiper stage. Simultaneously, stage 1 and the windshield washing pump are turned off. An electrical heating of the sensors I and II prevents the formation of ice at the electrodes.

By providing an additional sensor III (FIG. 9) having the same small electrode spacing as sensor I, it is possible to generate an ice-indicating signal. When water freezes, its electrical resistance increases. Accordingly, the electronic control circuit is designed to compare the measurements at sensor I and sensor III for indicating the formation of ice at sensor III.

Sensor I is electrically heated, to prevent the formation of ice on it. As a result, the electrical resistance at sensor I stays low.

Transistor Tr 9 converts the resistance value of sensor III into voltage values at P3. The multivibrator Tr 10 and Tr 11 turns on the light-emitting diode 1.

If there are water drops at sensor I and III, the light-emitting diode 1 becomes illuminated; the relay IV is not energized.

In the event of the formation of ice at sensor III and water at sensor I, the relay is energized by Tr 13 and Tr 14. The light-emitting diode 1 goes dark; light-emitting diode 2 lights up, and the electrical heating of the sensor III is initiated. The ice formed on sensor III melts; transistor Tr 12 blocks Tr 14, and relay IV switches off the heating for sensor III.

If when sensor III cools down ice again forms on it, relay IV is energized by Tr 13 and Tr 14; light-emitting diode 1 goes dark; light-emitting diode 2 lights up, and the electrical heating of sensor II is initiated. The operation is continually repeated, so that the light-emitting diode lights up repeatedly. The heat applied to sensor III and the heat lost by sensor III to the environment determine the on and off times of the light-emitting diodes.

Basically it is possible to use the sensor for the control of other arrangements, for example to control the intensity of fog lights.

Figure 9:
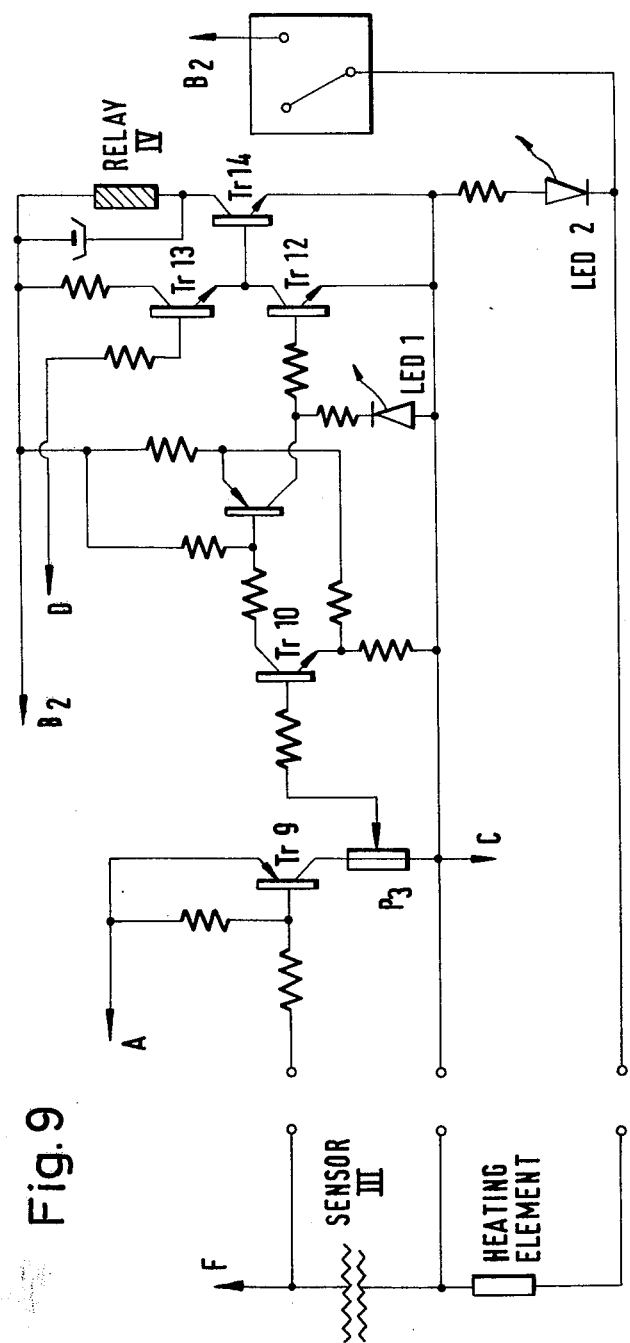
FIG. 9 is an auxiliary circuit for ice detection.

In FIGS. 8 and 9, reference characters A to F designate the various electrical connections.

Advantageously, each upwardly projecting tooth of the various lower sensor elements can be provided with a suction conduit for contributing to the leading off of water drops from the interelectrode space.

It will be understood that each of the elements described above, or two or more together, may also find a useful application in other types of circuits and configurations differing from the types described above.

While the invention has been illustrated and described as embodied in a particular control arrangement for controlling windshield wiping and washing, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In an arrangement for controlling the operation of a windshield wiper motor on a vehicle, in combination, at least one upper and one cooperating lower sensor element, each sensor element being comprised of a naked electrically conductive portion which adjoins the naked electrically conductive portion of the other sensor element of the pair of sensor elements to define an interelectrode gap, the naked electrically conductive portions being exposed to precipitation, the space between the electrically conductive portion of the upper sensor element and that of the lower sensor element being empty both between such conductive portions and also rearwardly of the interelectrode gap, so that precipitation bridging the interelectrode gap will not be supported from behind against the force of oncoming wind and thus not tend to become protractedly caught in the gap, the lower sensor element being of comb-like configuration and the naked electrically conductive portion of the lower sensor element comprising upwardly projecting comb teeth having pointed ends closely adjoining the naked electrically conductive portion of the upper sensor element, whereby water droplets bridging the interelectrode gap will tend not to cling to the electrically conductive portion of the lower sensor element because of the pointed configuration of the ends of the upwardly projecting comb teeth thereof; and circuit means operative for detecting the existence of precipitation by detecting the interelectrode gap resistance changes resulting from the bridging of the interelectrode gap by precipitation and in response to such detection generating a control signal for the windshield wiper motor.

2. The arrangement defined in claim 1, wherein the upper sensor element is of generally bar-shaped configuration.

3. The arrangement defined in claim 2, wherein the upper sensor element is tapered knife-like in rearwards and downwards direction along the longitudinal edge thereof which adjoins the teeth of the lower sensor element.

4. The arrangement defined in claim 3, wherein the upper sensor element is tapered in rearwards and upwards direction along the upper longitudinal edge thereof.

5. The arrangement defined in claim 1, wherein the naked electrically conductive portion of the upper sensor element is comprised of downwardly projecting teeth having pointed ends located opposite respective ones of the upwardly projecting teeth of the lower sensor element.

6. The arrangement defined in claim 5, wherein each of the downwardly projecting teeth of the upper sensor element has a downwardly and rearwardly extending front catching surface extending to its pointed end.

7. The arrangement defined in claim 6, wherein each of the downwardly projecting teeth of the upper sensor element has a back taper located opposite to the respective front catching surface.

8. The arrangement defined in claim 1, wherein the lower sensor element is rearwardly offset relative to the upper sensor element by a distance corresponding at least approximately to the thickness of the teeth.

9. The arrangement defined in claim 1, wherein each upwardly projecting tooth of the lower sensor element at the rear side thereof has a knife-like taper.

10. The arrangement defined in claim 1, wherein each upwardly projecting tooth of the lower sensor element has a lateral chamfer extending downwards and rearwards from the pointed end of the tooth.

11. The arrangement defined in claim 1, the lower sensor element occupying a general plane, and the upwardly projecting teeth of the lower sensor element being inclined relative to the vertical and lying in the general plane.

12. The arrangement defined in claim 1, the sensor elements being mounted for pivotal movement.

13. The arrangement defined in claim 1, the upper and lower sensor elements forming a first sensor unit, and further including a second sensor unit comprised of at least one pair of sensor elements having naked electrically conductive portions together defining an interelectrode gap, the interelectrode gap of the second sensor unit being of different size from that of the first sensor unit, whereby to make possible differentiation between different forms of precipitation, said circuit means being connected to the electrically conductive portions of the second sensor unit and operative for detecting interelectrode gap resistance changes of the second sensor unit.

14. The arrangement defined in claim 13, wherein the interelectrode gap of one of the sensor units is a horizontal interelectrode gap whereas the interelectrode gap of the other of the sensor units is a vertical interelectrode gap.

15. The arrangement defined in claim 1, further including means for heating the naked electrically conductive portions to prevent the formation of ice thereon.

16. The arrangement defined in claim 1, the control signal constituting a first control signal, wherein the circuit means includes time-delay means for generating a second control signal subsequent to the first control signal after the elapse of a predetermined time interval corresponding to a plurality of operating cycles of the windshield wiper motor.

17. The arrangement defined in claim 1, the circuit means further including means for generating a windshield washer activating signal in response to the detection of an interelectrode gap resistance change indicative of precipitation prior to the generation of the control signal, whereby to assure that the windshield is sufficiently wet prior to commencement of wiping to prevent dry wiping or smearing of the windshield in the event of light drizzle.

18. The arrangement defined in claim 1, the upper and lower sensor elements together forming a first sensor unit, further including an additional sensor unit configurated and dimensioned in correspondence to the first sensor unit, heating means for heating only the first sensor unit so as to permit the formation of ice on the additional sensor unit, and wherein the circuit means includes means for detecting the formation of ice by detecting the difference in the interelectrode gap resistances of the first and additional sensor units.

19. The arrangement defined in claim 1, wherein each of the upwardly projecting teeth of the lower sensor element is provided with a suction conduit.

* * * * *